United States Patent [19]

Eggensperger et al.

[11] 4,221,660

[45] Sep. 9, 1980

[54] METHOD FOR DISINFECTING

[75] Inventors: Heinz Eggensperger, Hamburg; Wolfgang Beilfuss, Hamburg-Hummelsbüttel; Wolfgang Zerling, Kaltenkirchen, all of Fed. Rep. of Germany

[73] Assignee: Sterling Drug Inc., New York, N.Y.

[21] Appl. No.: 7,497

[22] Filed: Jan. 29, 1979

Related U.S. Application Data

[62] Division of Ser. No. 852,579, Nov. 17, 1977, abandoned.

[51] Int. Cl.² .................................................. C02B 3/10
[52] U.S. Cl. .................................... 210/764; 210/758; 424/278; 424/317
[58] Field of Search ............... 422/5, 28, 29; 424/278, 424/317, 343; 210/62, 63 R, 64

[56] References Cited

U.S. PATENT DOCUMENTS

| | | | |
|---|---|---|---|
| 3,072,524 | 1/1963 | Gabelein | 21/58 X |
| 3,100,175 | 8/1963 | Bourquin | 21/58 X |
| 3,332,871 | 7/1967 | Robinson | 21/58 UX |
| 3,488,420 | 1/1970 | Keast et al. | 21/58 X |

FOREIGN PATENT DOCUMENTS

| | | | |
|---|---|---|---|
| 2300814 | 7/1973 | Fed. Rep. of Germany | 424/317 |
| 886188 | 1/1962 | United Kingdom | 21/58 |
| 1465727 | 3/1977 | United Kingdom | 21/58 |

*Primary Examiner*—Ferris H. Lander
*Attorney, Agent, or Firm*—Frederik W. Stonner; B. Woodrow Wyatt

[57] ABSTRACT

A method for disinfecting an aqueous system which comprises contacting the system with a solid aromatic percarboxylic acid having solubility in water not greater than about 1 weight-percent in a weight-percent amount in excess of said solubility in water; and a method for disinfecting materials with said aqueous system.

3 Claims, No Drawings

METHOD FOR DISINFECTING

This is a division of application Ser. No. 852,579, filed Nov. 17, 1977, now abandoned.

BACKGROUND OF THE INVENTION

1. Field of the Invention

The invention relates to a method for disinfecting aqueous systems contaminated with bacteria and/or fungi, e.g., industrial water circulation systems, which comprises contacting said systems with a solid aromatic percarboxylic acid as more fully defined hereinbelow. The invention further relates to a method for disinfecting materials contaminated with bacteria and/or fungi which comprises treating the material with an aqueous system which comprises a solid aromatic percarboxylic acid as more fully defined hereinbelow.

2. Description of the Prior Art

The antimicrobial activity of liquid percarboxylic acid formulations has been known for a long time. However, for certain applications it is desirable that the antimicrobially active agent exist in solid form and yield its active ingredient over a long period of time when in contact with the aqueous medium to be disinfected.

The solid aromatic percarboxylic acids employed as antimicrobial agents in the methods of the invention, as more fully described hereinbelow, belong to a well known class of compounds.

The stability of certain substituted perbenzoic acids, including a number of those employed in the methods of the invention, and their incorporation as bleaching agents in solid detergent compositions is described in British Patent Specification No. 886,188.

SUMMARY OF THE INVENTION

It has now been discovered that stable, solid organic percarboxylic acids which have solubility in water not in excess of about 1% are released slowly over a long period of time into aqueous systems with which they are placed in contact, resulting in antimicrobial activity of long duration in such aqueous systems.

Thus in one aspect of the invention there is provided a method for disinfecting an aqueous system contaminated with bacteria and/or fungi which comprises contacting the aqueous system with at least one solid aromatic percarboxylic acid having the formula

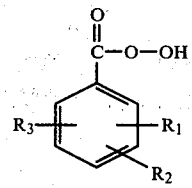

wherein $R_1$ and $R_2$ independently represent hydrogen or a radical selected from the group consisting of chloro, bromo, fluoro, nitro, cyano, trifluoromethyl, carboxyl, methoxycarbonyl, aminocarbonyl, alkyl having from 1 to 5 carbon atoms, phenyl, methoxy, ethoxy, acetoxy, acetyl and hydroxysulfonyl; and $R_3$ is a radical selected from the group consisting of those defined for $R_1$ and $R_2$; or $R_2$ and $R_3$ when taken together and attached to adjacent carbon atoms form, together with the ring to which they are attached, a naphthalene ring; where the solid aromatic percarboxylic acid has a solubility weight for weight in water not greater than about 1% and where the aqueous system is contacted with the aromatic percarboxylic acid in a weight-percent amount which is in excess of its solubility in water.

In another aspect of the invention there is provided a method for disinfecting a material contaminated with bacteria and/or fungi which comprises treating the material with an antibacterially and antifungally effective amount of an aqueous system where the aqueous system comprises at least one solid aromatic percarboxylic acid having the formula I wherein $R_1$, $R_2$ and $R_3$ have the meanings defined hereinbefore; where the solid aromatic percarboxylic acid has a solubility weight for weight in water not greater than about 1% and where the weight-percent amount of the solid aromatic percarboxylic acid in the aqueous system is in excess of its solubility in water.

When brought into contact with water or an aqueous system to be disinfected, some of the excess solid aromatic percarboxylic acid of formula I having the solubility properties defined hereinbefore is dissolved, thus providing efficient disinfection of the water or aqueous system. Despite the low degree of solubility of the solid aromatic percarboxylic acid of formula I, the amount dissolved in the water or aqueous system suffices to provide a wide spectrum of antimicrobial activity.

DETAILED DESCRIPTION INCLUSIVE OF THE PREFERRED EMBODIMENTS

Examples of specific stable, solid aromatic percarboxylic acids which can be employed in the methods of the invention are, for example, 4-cyanoperbenzoic acid, 4-tert-butylperbenzoic acid, 3-tert-butylperbenzoic acid, 2-tert-butylperbenzoic acid, 4-nitroperbenzoic acid, 4-fluoroperbenzoic acid, 3-chloroperbenzoic acid, 2,4-dichloroperbenzoic acid, 4-chloroperbenzoic acid, 4-methoxyperbenzoic acid, 2-methylperbenzoic acid, 3-methylperbenzoic acid, 4-methylperbenzoic acid, 3,4,5-trimethoxyperbenzoic acid, monoperphthalic acid and pernaphthoic acid.

Particularly preferred are 4-tert-butylperbenzoic acid, 3-chloroperbenzoic acid, 4-methylperbenzoic acid and 4-methoxyperbenzoic acid. Perbenzoic acid, on the other hand, is not suited since it is not sufficiently stable, being storable only at <0° C. At room temperature perbenzoic acid, both as a solid and in solution, tends to decompose.

The solid stable percarboxylic acids of formula I which are employed in the methods of the invention can be used either singly or in mixtures with each other. Furthermore, they can be admixed with other poorly water soluble antimicrobially active substances and, if desired, with inert carriers. A suitable poorly water soluble antimicrobially active substance, e.g., is sorbic acid. As carriers for the aromatic percarboxylic acids, there can be used the related aromatic carboxylic acids, or other poorly soluble aromatic carboxylic acids, as well as, for example, active carbon, silica gel, poorly water soluble inorganic salts such as calcium fluoride, calcium sulfate, barium sulfate, etc., and other difficulty soluble solid materials which are resistant to oxidation by the aromatic percarboxylic acids.

In addition, if desired, additives such as corrosion inhibitors, e.g. 4-tert-butylbenzoic acid, may be admixed with the percarboxylic acid.

For use in the disinfection of water and aqueous systems, the aromatic percarboxylic acids, in admixture with carriers and additives if desired, can be employed as powders, tablets, granulates, formed solid bodies, or surface coatings. They also can be placed in water-permeable bags or precipitated on sieves and filters in which forms they are particularly suited for disinfecting industrial water circulations systems, by e.g. suspending the water-permeable bag in the flow system or by passing the circulation water through the filters or sieves.

Furthermore, by suspending the percarboxylic acid-containing sieves or bags into water storage tanks, water free of viable bacteria results after a short time interval. Also, make-up for the storage tanks becomes free of viable bacteria after a short period of time. Since the resulting water has dissolved therein sufficient antimicrobially active percarboxylic acid, it can be used for disinfecting medical instruments as well as articles of daily use, such as e.g. nipples for baby bottles and baby bottles thus facilitating the disinfection and sterilization of such utensils in a simple and completely unobjectionable manner.

The antimicrobial percarboxylic acids of formula I employed in the methods of this invention can be placed in contact with the water or aqueous systems to be disinfected continually or periodically. Even with a single brief contact of the percarboxylic acid with the aqueous system, an adequate antimicrobial effect is realized and it is not necessary that the peracid content of this system reach saturation.

A particularly active percarboxylic acid for the purposes of the methods of this invention is 4-tert-butylperbenzoic acid which can be prepared by the reaction of 4-tert-butylbenzoic acid with high percentage hydrogen peroxide in presence of a non-oxidizable strong acid, e.g. methanesulfonic acid, or by reaction of 4-tert-butylbenzoic chloride with sodium hydroxide/hydrogen peroxide. 4-tert-Butylperbenzoic acid is a colorless crystalline compound which melts at about 81° C. It has a characteristic faint odor which can be masked by a perfume. 4-tert-Butylperbenzoic acid is surprisingly stable. Two test samples stored at room temperature for 6 months assayed as follows:

Test sample 1: Initial assay: 65% peracid; after 6 months: 63.5% peracid
Test sample 2: Initial assay: 15.5% peracid; after 6 months: 15.5% peracid 4-tert-Butylperbenzoic acid is only sparingly soluble in water. An investigation of its solubility, stability and antimicrobial activity is described below. The microorganisms used in the microbiological test procedures are identified hereinbelow by roman numerals as follows:

I. *Staphylococcus aureus*
II. *Klebsiella pneumoniae*
III. *Pyogenes*
IV. *Proteus vulgaris*
V. *Trichophyton mentagrophytes*
VI. *Candida albicans*
VII. *Aspergillus niger*
VIII. *Bacillus subtilis*
IX. *Mycobacterium smegmatis*
X. *Escherichia coli* p-tert-Butylperbenzoic acid (1 g.) was suspended in 100 g water (softened) resulting in a saturated solution containing a solid residue. After one day, the residue was filtered off and resuspended anew in water. The filtrate was assayed for its peracid content and its bacteriological activity. An assay of 0.02 weight % 4-tert-butylperbenzoic acid was obtained. The microbiological test results summarized in Table 1 below were obtained in suspension, germ carrier and surface tests according to DGHM (Richtlinien für die Prüfung Chemischer Desinfektionsmittel, 3. Aufl., Gustav Fischer Verlag, Stuttgart) (Guidelines for testing of chemical disinfecting agents, 3rd ed., Gustav Fischer publishers, Stuttgart). Filtration again was carried out after 5 and 6 days, respectively, the residue again resuspended and the filtrate assayed for peracid. In each case an assay of 0.02% weight % peracid was found. After 41 days, the system was filtered again and the residue was again resuspended. The filtrate still assayed for 0.02 weight-percent peracid. The bacteriological assay gave the following values:

| Suspension Test According to DGHM | | | | |
|---|---|---|---|---|
| Conc. | I | II | III | IV |
| conc. | 2 ½' | 2 ½' | 5' | 2 ½' |
| 50 | 2 ½' | 2 ½' | 15' | 5' |
| 25 | 30' | 30' | >30 | 5' |

After 200 days, the percarboxylic acid solution in contact with the solid residue still assayed 0.02 weight %.

Table 1

| | Aqueous 4-tert-Butylperbenzoic acid Solution (with solid phase) | | | | | | | | | Surface | | | |
|---|---|---|---|---|---|---|---|---|---|---|---|---|---|
| | | | | | | | | Germ Carrier | | I | | X | |
| | Suspension, Bacteria | | | | Suspension, Fungi | | | Garnets | Cambrie | Wood | | Wood | |
| Conc. | I | II | III | IV | V | VI | VII | VIII | IX | PVC | Enamel | PVC | Enamel |
| 1 | >30' | >30' | >30' | >30' | >30' | >30' | >30' | | | | | | |
| 2 | >30' | >30' | >30' | >30' | 15' | >30' | >30' | | | | | | |
| 5 | 5' | >30' | >30' | >30' | 5' | >30' | >30' | | | | | | |
| 10 | 2 ½' | >30' | >30' | >30' | 2 ½' | 15' | >30' | | >120' | | | | |
| 25 | 2 ½' | 30' | >30' | 5' | 2 ½' | 2 ½' | >30' | | 60' | | | | |
| 50 | 2 ½' | 2 ½' | 15' | 5' | | | | >6$^h$ | 15' | | | | |
| conc. | 2 ½' | 2 ½' | 5' | 2 ½' | | | | >6$^h$ | 15' | >6$^h$ | >6$^h$ | >6$^h$ | >6$^h$ |
| + 20% Serum | | | | | | | | | | | | | |
| 50 | >30' | >30' | >30' | >30' | | | | | | | | | |
| 80 | >30' | >30' | >30' | >30' | | | | | | | | | |

An aqueous 3-chloroperbenzoic acid solution with solid phase present also was tested in the suspension, germ carrier and surface tests according to DGHM. The results are summarized in Table 2 below.

Table 2

| | Aqueous 3-Chloroperbenzoic acid Solution (with solid phase) | | | | | | | | | Surface | | | |
|---|---|---|---|---|---|---|---|---|---|---|---|---|---|
| | | | | | | | | | Germ Carrier | | I | | X | |
| | Suspension, Bacteria | | | | Suspension, Fungi | | | Garnets | Cambric | | Wood | | Wood |
| Conc. | I | II | III | IV | V | VI | VII | VIII | IX | PVC | Enamel | PVC | Enamel |
| 1 | >30' | >30' | >30' | 5' | 2½' | 5' | >30' | | | | | | |
| 2 | 15' | 5' | >30' | 2½' | 2½' | 5' | >30' | | | | | | |
| 5 | 2½' | 2½' | 15' | 2½' | 2½' | 2½' | 5' | | | | | | |
| 10 | 2½' | 2½' | 5' | 2½' | 2½' | 2½' | 2½' | $1^h$ | 15' | | | | |
| 25 | | | | | | | | $1^h$ | 15' | >$6^h$ | >$6^h$ | >$6^h$ | >$6^h$ |
| 50 | | | | | | | | $1^h$ | 15' | >$6^h$ | >$6^h$ | $2^h$ | $6^h$ |
| conc. | | | | | | | | $1^h$ | 15' | >$6^h$ | $6^h$ | $1^h$ | $4^h$ |
| +20% Serum | | | | | | | | | | | | | |
| 25 | >30' | >30' | >30' | >30' | | | | | | | | | |
| 50 | 2½' | >30' | >30' | 2½' | | | | | | | | | |
| 80 | 2½' | 2½' | >30' | 2½' | | | | | | | | | |

We claim:

1. A method for disinfecting an aqueous system contaminated with bacteria and/or fungi which comprises contacting the aqueous system with at least one solid aromatic percarboxylic acid having the formula

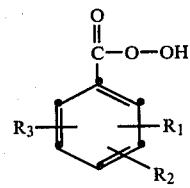

where $R_1$ and $R_2$ independently represent hydrogen or a radical selected from the group consisting of chloro, bromo, fluoro, nitro, cyano, trifluoromethyl, carboxyl, methoxycarbonyl, aminocarbonyl, alkyl having from 1 to 5 carbon atoms, phenyl, methoxy, ethoxy, acetoxy, acetyl and hydroxysulfonyl; and $R_3$ is a radical selected from the group consisting of those defined for $R_1$ and $R_2$; or $R_2$ and $R_3$ when taken together and attached to adjacent carbon atoms form, together with the ring to which they are attached, a naphthalene ring; where the solid aromatic percarboxylic acid has a solubility weight for weight in water not greater than about 1% and where the aqueous system is contacted with a weight-percent amount of the aromatic percarboxylic acid which is in excess of its solubility in the aqueous system.

2. A method according to claim 1 wherein the aromatic percarboxylic acid is selected from the group consisting of 4-cyanoperbenzoic acid, 4-tert-butylperbenzoic acid, 3-tert-butylperbenzoic acid, 2-tert-butylperbenzoic acid, 4-nitroperbenzoic acid, 4-fluoroperbenzoic acid, 3-chloroperbenzoic acid, 2,4-dichloroperbenzoic acid, 4-chloroperbenzoic acid, 4-methoxyperbenzoic acid, 2-methylperbenzoic acid, 3-methylperbenzoic acid, 4-methylperbenzoic acid, 3,4,5-trimethoxyperbenzoic acid, monoperphthalic acid and pernaphthoic acid.

3. A method according to claim 2 wherein the aromatic percarboxylic acid is selected from the group consisting of 4-tert-butylperbenzoic acid, 3-chloroperbenzoic acid, 4-methylperbenzoic acid and 4-methoxyperbenzoic acid.

* * * * *

UNITED STATES PATENT AND TRADEMARK OFFICE
CERTIFICATE OF CORRECTION

PATENT NO. : 4,221,660

DATED : September 9, 1980

INVENTOR(S) : Heinz Eggensperger et al.

It is certified that error appears in the above—identified patent and that said Letters Patent is hereby corrected as shown below:

On the cover sheet after Item [22], add Item [30]

November 26, 1976    Germany    2,653,738

Signed and Sealed this

Fifth Day of May 1981

[SEAL]

Attest:

RENE D. TEGTMEYER

*Attesting Officer*    *Acting Commissioner of Patents and Trademarks*